United States Patent [19]

Tweed et al.

[11] 3,945,373
[45] Mar. 23, 1976

[54] TOCODYNAMOMETER

[75] Inventors: David G. Tweed, Stoneham, Mass.; Eric LaWhite, South Royalton, Vt.

[73] Assignee: Brattle Instrument Corporation, Cambridge, Mass.

[22] Filed: Nov. 21, 1974

[21] Appl. No.: 525,945

[52] U.S. Cl. .............................. 128/2 S; 128/2.05 P
[51] Int. Cl.² .......................................... A61B 5/10
[58] Field of Search ........ 128/2 K, 2 R, 2 S, 2.05 E, 128/2.05 P, 2.05 R, 2.05 S, 2.05 T, 2.08

[56] References Cited
UNITED STATES PATENTS

| 2,294,015 | 8/1942 | Salb et al. | 128/2.05 S |
| 2,702,354 | 2/1955 | Chorpening | 128/2.05 P |
| 3,154,066 | 10/1964 | Grindheim et al. | 128/2.05 P |
| 3,181,528 | 5/1965 | Brackin | 128/2 K |
| 3,483,861 | 12/1969 | Tiep | 128/2.08 |
| 3,704,708 | 12/1972 | Iberall | 128/2.05 P |

Primary Examiner—William E. Kamm

[57] ABSTRACT

A tocodynamometer for providing an electrical output related to body surface displacement of a patient, comprising, a housing, a patient contacting member, a support assembly mounting the member for controlled movement relative to the housing in response to the displacement, and an electro-optical transducer assembly for converting the controlled movement into the electrical output, the transducer assembly comprising relatively movable members one of which is coupled to the patient contacting member for movement therewith to vary the output in response to the controlled movement. In another aspect the support assembly comprises at least one planar spring element having a first portion fixed to the housing and a second portion fixed to the member.

1 Claim, 4 Drawing Figures

TOCODYNAMOMETER

BACKGROUND OF THE INVENTION

This invention relates to measurement of uterine contrations or other biological phenomena involving displacement of an external body surface.

A tocodynamometer for making such measurements typically involves a movable patient contacting member and a transducer for converting displacement into an electrical output.

Summary of the Invention

The invention provides a rugged, inexpensive, accurate, easily used tocodynamometer in which sensitivity can be adjusted and in which the design permits wide choice of the relationship between electrical output and body surface displacement. The unit is stable under temperature changes, and the mechanical arrangement for sensing displacement is virtually frictionless and highly resistant to mechanical overload while providing excellent force versus displacement characteristics.

In general the invention features a tocodynamometer for providing an electrical output related to body surface displacement of a patient, comprising, a housing, a patient contacting member, a support assembly mounting the member for controlled movement relative to the housing in response to the displacement, and an electrooptical transducer assembly for converting the controlled movement into the electrical output, the transducer assembly comprising relatively movable members one of which is coupled to the patient contacting member for movement therewith to vary the output in response to the controlled movement. In another aspect the support assembly comprises at least one planar spring element having a first portion fixed to the housing and a second portion fixed to the member. In preferred embodiments the support assembly comprises a pair of phosphor bronze spring elements which are generally circular and parallel to each other, a first spacer is mounted between central portions of the spring elements, and a second spacer is mounted between outer portions of the elements, the elements being cut away between the spacers to facilitate relative movement of the spacers along an axis perpendicular to the planes of the elements, the patient contacting member being connected to the first spacer; the transducer assembly comprises a subassembly comprising a light source and a photosensitive detector arranged to receive light from the source along a path, and an interrupter mounted to extend into the path, the subassembly or the interrupter being coupled to the support for the movement therewith to vary the extent of the interrupter into the path and hence to vary the amount of light received by the detector; the spacers have black surfaces defining walls of a light chamber, the transducer assembly being mounted in the chamber; and the patient contacting member is adjustable relative to the support assembly, through an external knob, for setting the initial position of the member relative to the housing, thereby determining the operating range of the tocodynamometer.

BRIEF DESCRIPTION OF THE DRAWINGS

FIGS. 4–5 are exploded views showing portions of the tocodynamometer of FIG. 1.

DESCRIPTION OF THE PREFERRED EMBODIMENT

Figure 1:
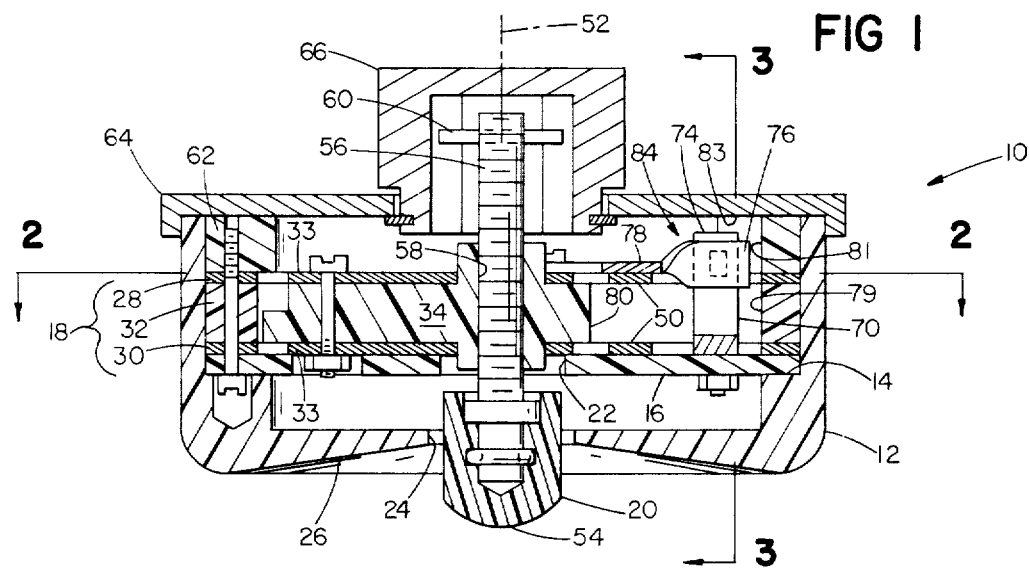
FIG. 1 is a vertical sectional view of a tocodynamometer embodying the invention.
Figure 2:
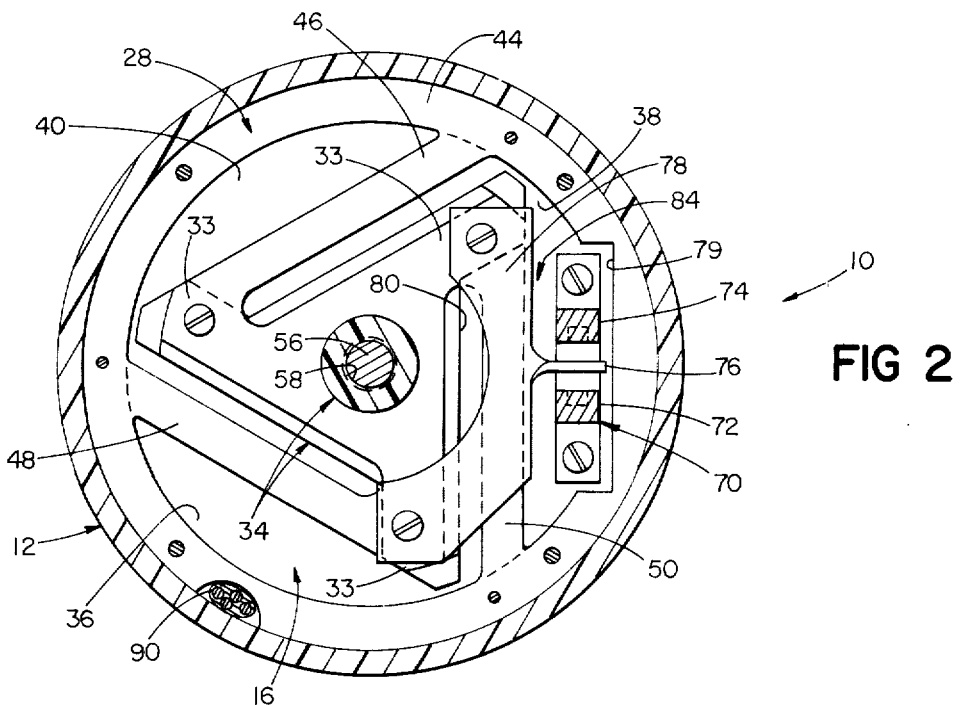
FIG. 2 is a sectional view taken along 2—2 of FIG. 1.

Referring to the drawings, tocodynamometer 10 has a plastic housing 12 in which are mounted, on generally annular ledge 14, printed circuit board 16 and resilient support assembly 18 from which extends, through openings 22 and 24 in board 16 and concave bottom wall 26 of the housing, respectively, plastic patient-contacting pin 20.

Support 18 has two identical phosphor bronze planar spring members 28 and 30, attached at their rims to opposite sides of a generally annular plastic spacer 32, and attached at their central portions 33 to opposite sides of a generally triangular plastic spacer 34. Elements 28 and 30 have cutouts 36, 38, and 40 arranged so that in each element central portion 33 is connected to outer portion 44 through three resilient legs 46, 48, and 50, to permit displacement of spacer 34 relative to spacer 32 along central axis 52 of pin 20.

Pin 20 has a rounded patient-contacting surface 54 and extends from screw 56 which is threaded in central opening 58 of spacer 34, and has a transverse pin 60 through its end opposite surface 54.

Plastic retaining ring 62 is aligned with spacer 32 above element 28, and housing cover 64 holds ring 62, support assembly 18, and circuit board 16 tightly against ledge 14. Screw 56 extends into external adjustable knob 66 mounted on the cover, and pin 60 couples the screw to the knob, so that by rotation of the knob the initial position of pin surface 54 relative to the bottom of housing 12 may be set.

Electro-optical transducer assembly 70 consists of a light emitter 72 and photosensitive detector 74 (e.g., Photon Coupled Interrupter Module H 13Al sold by General Electric) mounted on circuit board 16 and extending upwardly through cutouts 38 in elements 28 and 30, beyond spacers 32 and 34. Light interrupter 76 extends from bracket 78 mounted on element 28 and screwed to spacer 34, into the space between emitter 72 and detector 74. Interrupter 76 is a finger shaped to interrupt a fraction of the light passing from emitter to detector, the fraction depending upon the position of the finger along axis 52. The walls 78 and 80 of spacers 32 and 34 which surround the transducer assembly 70, inner walls 81 and 83 of ring 62 and cover 64, respectively (walls 78, 80, 81, and 83 in effect defining a light chamber 84), as well as finger 76 and the inactive exterior surfaces of emitter 72 and detector 74, are black to minimize light reflection.

Electrical cord 90 connects emitter 72 and detector 74 to an appropriate monitoring and power supply unit 100, through conventional circuitry on board 16.

Figure 3:
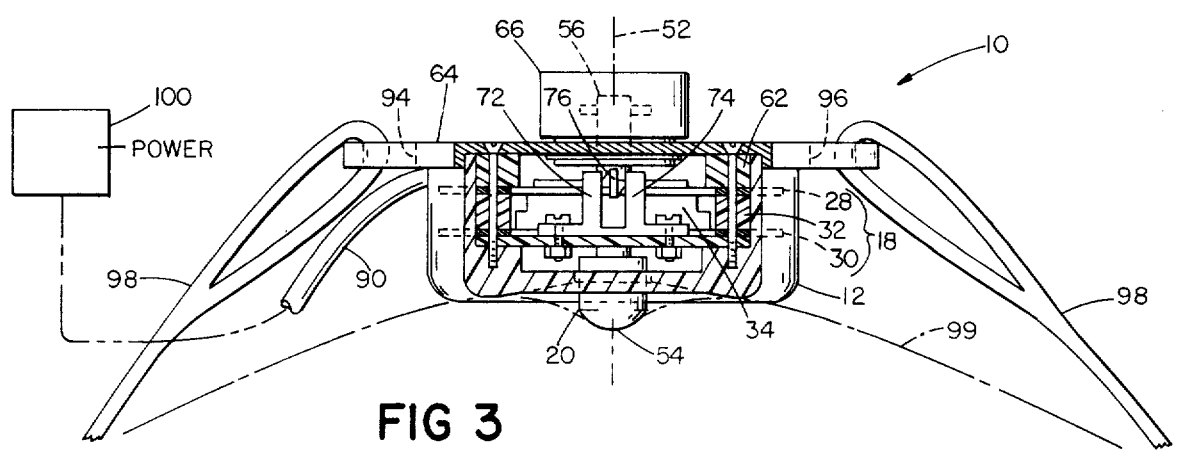
FIG. 3 is a view of the tocodynamometer of FIG. 1 in use against a patient's abdomen, with a monitor shown schematically, and with the tocodynamometer shown in a sectional view taken along 3—3 of FIG. 1.
Figure 4:
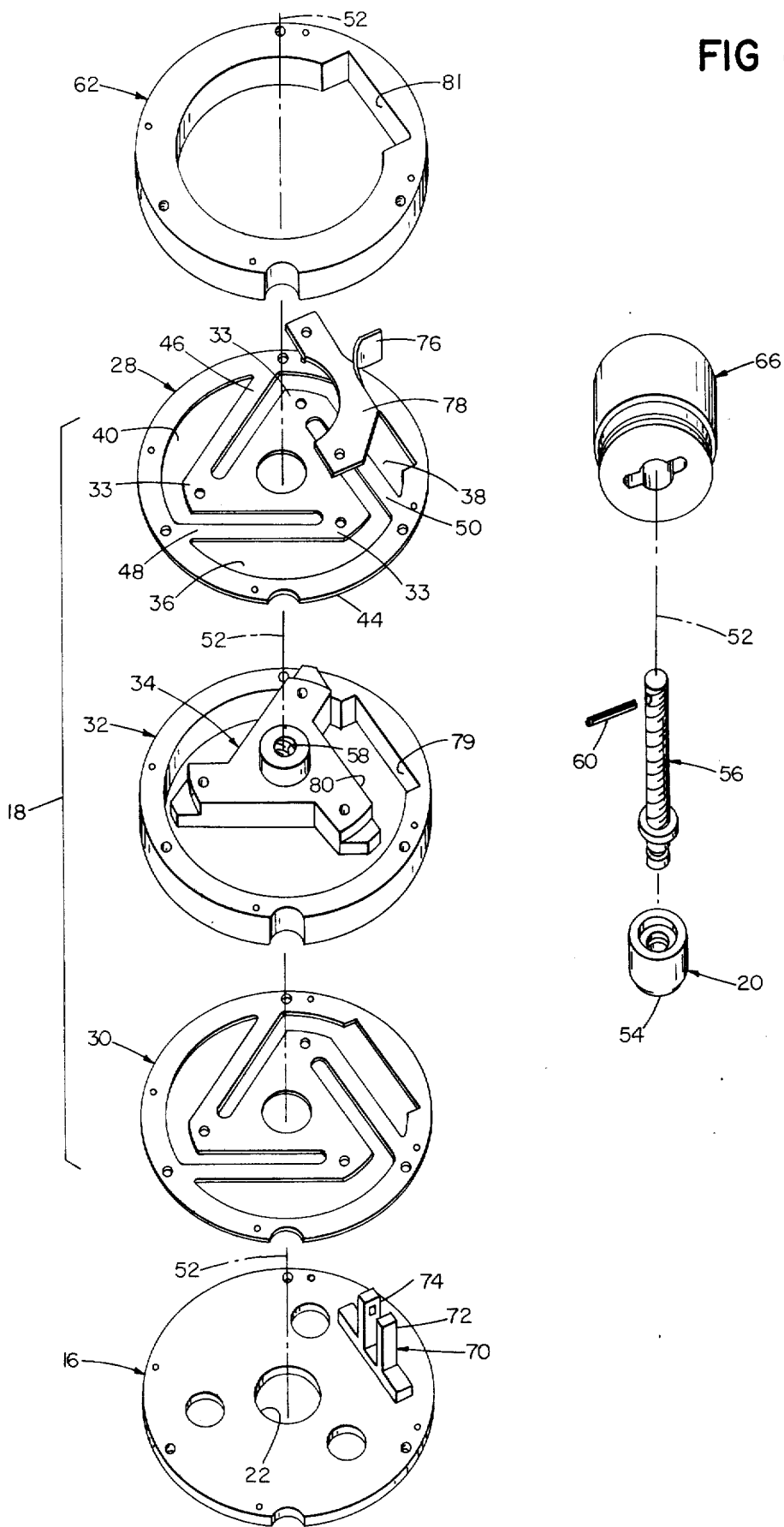

Cover 64 has slots 94 and 96 through which strap 98 extends, for connection of the tocodynamometer to the abdomen 99 of a patient as shown in FIG. 3.

In operation, uterine contractions will exert pressure on surface 54 of pin 20, pushing the pin upwardly against the spring force of elements 28 and 30, causing displacement of finger 76 and thus changing the amount of light from emitter 72 which is received by detector 74. The electrical signal produced by detector 74 and read out by unit 100 is thus dependent upon the position of finger 76 and represents an analog measurement of the uterine contraction. A wide variety of functions of output versus displacement of pin 20 may be generated by appropriate selection of the shape of finger 76. Adjustment of knob 66 determines the operating range of the device.

Other embodiments (e.g., the use of a variable density filter material for finger 76, etc.) are within the following claims.

What is claimed is:

1. A tocodynamometer for providing an electrical output related to body surface displacement of a patient, comprising a housing, a resilient support assembly having a pair of planar, parallel, generally circular spring elements having opposing surfaces, an outer, generally annular spacer mounted between said spring elements and fixed to said housing, and an inner spacer extending between said opposing surfaces of said spring elements inwardly of said outer spacer, said spacers being separated from each other so that said inner spacer is resiliently movable relative to said housing along an axis, said spring elements having cutouts in planar portions between said spacers, said spacers having opposing wall portions generally parallel to said axis which comprise side walls of a light chamber, a patient contacting member having a shaft extending along said axis, said shaft being threaded and extending through a correspondingly threaded opening in said inner spacer, said shaft having a patient contacting surface at one end and a knob on the other end, said knob being external to said housing to permit rotation of said threaded shaft in said threaded opening and hence adjustment of the initial position of said surface relative to said housing while said tocodynamometer is in position on a patient, thereby determining the operating range of said tocodynamometer, and a transducer assembly mounted inside said housing and comprising a light source and a photosensitive detector mounted in spaced positions fixed relative to said housing and extending through a said cutout between said spacers into said light chamber, with said detector being arranged to receive light from said source along a path, and a rigid interrupter finger rigidly mounted on said movable inner spacer for movement therewith along said axis, said finger having a permanently shaped portion arranged to extend in said light chamber and into said path between said source and said detector, whereby the amount of light from said source received by said detector will vary as a function of the position of said finger along said axis, said function being determined by the shape of said shaped portion.

* * * * *